United States Patent [19]

Herndon, Jr. et al.

[11] Patent Number: 5,420,369
[45] Date of Patent: May 30, 1995

[54] CHLOROALKYLATION OF AROMATIC COMPOUNDS

[75] Inventors: R. Carl Herndon, Jr.; Gary D. Focht; Karl R. Jones, all of Baton Rouge, La.

[73] Assignee: Albemarle Corporation, Richmond, Va.

[21] Appl. No.: 276,584

[22] Filed: Jul. 18, 1994

[51] Int. Cl.$^6$ .................. C07C 17/10; C07C 17/12; C07C 25/00
[52] U.S. Cl. .................. 570/191; 570/190; 570/192
[58] Field of Search .................. 570/190, 191, 192

[56] References Cited

U.S. PATENT DOCUMENTS

| | | | |
|---|---|---|---|
| 2,573,394 | 10/1951 | Gottfried et al. | 570/191 |
| 3,911,033 | 10/1975 | Schaffner et al. | 570/191 |
| 4,191,711 | 3/1980 | Lentho et al. | 570/191 |
| 4,536,595 | 8/1985 | Gardano et al. | 570/191 |

Primary Examiner—Werren B. Lone
Attorney, Agent, or Firm—Philip M. Pippenger

[57] ABSTRACT

The co-formation of diarylalkane by-product in the chloroalkylation of an aromatic compound with an aldehyde is minimized by conducting the reaction in a continuous manner in a concentration with agitation and in the presence of both hydrogen sulfate and hydrogen chloride.

19 Claims, No Drawings

CHLOROALKYLATION OF AROMATIC COMPOUNDS

FIELD OF THE INVENTION

This invention relates to a process for chloroalkylating aromatic compounds to form 1-chloro-1-arylalkanes.

BACKGROUND

As disclosed in March, *Advanced Organic Chemistry*, Second Edition, McGraw-Hill, New York, 1977, pp. 501–502; Olah, *Friedel-Crafts and Related Reactions*, Volume 2, Interscience Publishers, New York, 1963–1964, pp. 659–784; U.S. Pat. No. 2,516,971 (Galigzenstein et al.); Canadian Patent 1,135,268 (Harris); and the references cited therein, it is known that aromatic compounds can be haloalkylated by reacting them with a hydrogen halide and an appropriate aldehyde, or with an α-halo-alkyl ether or an α-haloalkyl alkyl ether, in the presence of a Lewis acid or a proton acid as a catalyst, most commonly in the presence of zinc chloride.

The haloalkylations utilizing formaldehyde or a formaldehyde-derived ether have been successfully employed in providing fairly high yields of 1-halo-1-arylalkanes. Reasonably high yields of 1-halo-1-arylalkanes have sometimes also been obtained from haloalkylations utilizing higher aldehydes or ethers derived from them. However, it has frequently not been found possible to provide commercially acceptable yields of 1-halo-1-arylalkanes from higher aldehydes and ethers, especially when the aromatic compound has been one of the less reactive ones, such as a monoalkylaromatic hydrocarbon. There has been too much co-formation of diarylalkane by-product.

It would be desirable to find a way of increasing the 1-halo-1-arylalkane yields obtainable from such processes to provide a more economical method of preparing, the 1-halo-1-(4-alkyl-phenyl)alkanes used in known processes, such as those of U.S. Pat. No. 4,536,595 (Gardano et al.), Canadian Patent 1,197,254 (Francalanci et al.), British Patent 1,560,082 (Dynamit Nobel), Czechoslovakian Certificate of Authorship 219,752 (Palecek et al.), and Japanese Kokai 47-39050 (Miyatake et al.) and 51-111536 (Tokutake).

Definitions

As used herein, alkyl means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 1-ethylhexyl, 1,1,3,3-tetramethylbutyl, nonyl decyl, dodecyl, tetradecyl, hexadecyl, octadecyl and eicosyl;

substituted phenyl and substituted naphthyl means
phenyl or naphthyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, haloalkyl which means straight or alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoro-methyl, 2,2,2-trifluoroethyl, 2,3,3-trifluoropropyl, 1,1,2,2-tetrafluoroethyl and 2,2,3,3-tetrafluoropropyl;

phenylalkyl means that the alkyl moiety is straight or branched chain alkyl having 1 to 8 carbon atoms and includes, for example, benzyl, 2-phenylethyl, 1-phenylethyl, 3-phenylpropyl, 4-phenylbutyl, 5-phenylpentyl, 6-phenylhexyl and 8-phenyloctyl; and substituted phenylalkyl means the above-mentioned phenylalkyl which is substituted by at least one substituent selected from the group consisting of halogen, amino, nitro, hydroxy, alkyl, alkoxy and haloalkyl on the phenyl nucleus.

The Invention

It has now been found that 1-chloro-1-arylalkanes can be continuously prepared with minimum co-formation of the diarylalkane by-product, even when the aromatic reactant is a monoalkyl-aromatic hydrocarbon, by adding one molar proportion of an aromatic compound having at least one free ring position to from about 0.1 to about 1.5 mol of an aldehyde with agitation at a temperature in the range of about −35° C. to about 0° C. and in the presence of at least one molar proportion of hydrogen chloride and about 2–15 molar proportions of hydrogen sulfate.

The addition of the above-named components form a reaction mixture from which is removed a reaction effluent stream. This stream is comprised of unreacted starting materials (typically about 40% to about 60% of the starting material is not converted), the desired aryl-substituted ethyl halide (also termed herein as a 1-halo-1-arylalkane) and higher molecular weight by-products such as dimers, trimers and the like. Typically, the by-product produced in greatest yield is the dimer, e.g., where benzene is used as the aromatic compound and acetaldehyde as the aldehyde in the presence of hydrogen chloride and hydrogen sulfate, the dimer is 1,1-diphenylethane.

It has been discovered that if the rate of addition of all of the components is adjusted to provide a mixture of the above-named components in the ranges indicated (and the removal of a quantity of the reaction mixture is held substantially equal to the rate of addition of the reactants), then the amount of desired chloralkylated product is maximized while minimizing the quantity of higher molecular weight by-products—typically dimer. As such, when mixtures of the components are employed outside the ranges indicated, the yield of chloroalkylated product diminishes and the ratio of chloroalkylated product to dimer is seen to decrease. Within the ranges noted, the yields and ratios reach a substantially constant value. Thus, preferred ranges are about 0.1 to 1.5 mol of acetaldehyde per mol of the aromatic compound. Outside of the range and preferred range disclosed, variability of yield and ratio during the course of reaction effluent stream removal occurs.

Further, if the continuous removal of reaction effluent stream does not occur, i.e., a batch reaction, yields of product and ratio of product to by-product decrease dramatically.

The aromatic compound employed in the practice of the invention may be a carbocyclic aromatic compound, e.g., an unsubstituted aromatic hydrocarbon, such as benzene, naphthalene, anthracene, phenanthrene, etc.; a polyalkylaromatic hydrocarbon such as xylene, pseudo-cumene, mesitylene, etc.; and aromatic hydrocarbon bearing a substituent such as halo, cyano, nitro, hydroxy, alkoxy, phenoxy, alkylthio, etc. (e.g., the 2-, 3-, and 4-chloronitrobenzenes, the 2-, 3-, and 4-fluoronitrobenzenes, 4-chloronitrobiphenyl, 6-methoxynaphthalene, phenoxybenzene, etc.); or it may be a heterocyclic aromatic compound, such as a chlorocarbazole, 2-phenyl-1-isoindolinone, 6-fluoro-5-nitroquinoline, etc. However, because of the commercial interest in their haloalkylated products and the difficulty that has previously been encountered in preparing the desired 1-halo-1-arylalkanes, the preferred aromatic compounds are monoalkylaromatic hydrocarbons, such as substituted phenyl or substituted naphthyl illustrated by 1-methylnaphthalene, 2-methylnaphthalene, 2-methoxynaphthalene, and the various monoalkylbenzenes, e.g., the methyl-, ethyl, propyl-, isobutyl-, sec-butyl-, t-butyl-, isopentyl-, t-pentyl-, and hexylbenzenes. The most preferred aromatic compounds are the monoalkylbenzenes wherein the alkyl group contains 1–5 carbons.

The aldehydes of use herein have the formula

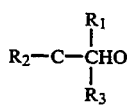

where $R_1$, $R_2$ and $R_3$ are the same or different and are hydrogen, alkyl, phenylalkyl or substituted phenylalkyl. Preferably, $R_1$ is alkyl having 1 to 10 linear or branched carbon atoms and $R_2$ and $R_3$ are the same as $R_1$ or are hydrogen. Most preferably, $R_1$ has 1 to 6 carbon atoms and $R_2$ and $R_3$ are hydrogen. Particularly preferred is where $R_1$ is alkyl of 1 to 3 carbon atoms. Acetaldehyde is a very useful reactant in the process of the present invention.

The amount of aldehyde employed in the chloroalkylation reaction may be the stoichiometric amount, i.e., the amount which provides one $R_1$ group per molecule of aromatic hydrocarbon. In some cases, less than this amount may be employed. However, it is generally preferred to employ an amount that provides at least one $R_1$ group per molecule of aromatic compounds. Most preferred is about one mole of such aldehyde per mole of haloalkylated product. There does not appear to be any maximum to the amount of aldehyde that may be used other than the maximum that economics permit.

As in known processes, the chloroalkylation is conducted in the presence of an acid catalyst, preferably hydrogen sulfate. In order to avoid the presence of too much water in the reaction mixture, as well as to take advantage of commercially-available materials, the hydrogen sulfate is generally introduced in the form of 88–98% sulfuric acid. The amount employed is generally such as to provide at least about one mol, preferably at least about 2–6 moles, per mol of aromatic compound; and it ordinarily should not exceed about 15 moles per mol of aromatic compound. It should be noted that oleum may be used and directly added to the reaction mixture. It combines with the water produced in the reaction to yield sulfuric acid at the desired concentration.

The amount of hydrogen chloride used in the reaction is usually at least about one equivalent, based on the amount of aromatic compound; and it is generally introduced by bubbling it through the reaction mixture or by pressurizing the reaction vessel with it.

Since improved yields of 1-chloro-1-arylalkane are not obtained without it, the use of the hydrogen chloride is critical.

The reaction is usually conducted at a reaction temperature in the range of about $-35°$ C. to about $0°$ C., preferably about $-35°$ C. to about $-15°$ C., most preferably about $-30°$ C. to about $-20°$ C., in order to achieve the maximum advantages of the invention. The higher temperatures generally favor higher conversions, while the lower temperatures are apt to favor higher chloroalkylation product/diarylalkane ratios.

The manner of combining the ingredients does appear to be somewhat important. For example, (1) the aldehyde may be dissolved in the aromatic compound and added to the catalyst while bubbling hydrogen chloride through the reaction mixture, or (2) the pure or crude aldehyde, the aromatic compound, and the catalyst may be combined in either fashion in a reaction vessel which is pressurized with the hydrogen chloride, etc. However, the best addition method is to add all reactants to a well-mixed stream of reaction mixture.

The invention is useful as an alternative method of preparing 1-chloro-1-arylalkanes from aromatic compounds that are known to be capable of providing high yields of such products by known chloroalkylation techniques. However, it is particularly advantageous as a method of preparing 1-chloro-1-arylalkanes from the less reactive aromatic hydrocarbons, such as monoalkyl-benzenes, that have not previously been found to be capable of providing high yields of such products by chloroalkylation processes other than chloromethylations.

It should be noted that the process of the present invention is most preferably operated in a continuous, stirred reaction. Disadvantageously, when the process is performed in a continuous plug flow reaction rather than observing improved yields of haloalkylated product, depressed yields are obtained, closely paralleling semi-batch systems.

As is known, the products obtained by the process are useful as internal standards, intermediates for the preparation of monomers, detergents, pharmaceuticals, etc. When they are used as chemical intermediates, they may be subjected to the same reactions as have previously been used to convert them to desired products. For example, the 1-chloro-1-phenylethanes can be dehydrohalogenated in any known manner to provide styrenes which can then be polymerized by known techniques.

A particularly interesting application of the 1-chloro-1-(4-alkylphenyl)ethanes which are prepared in a preferred embodiment of the invention is as intermediates for the preparation of ibuprofen and related pharmaceuticals. When they are used in such applications, they may be converted to the desired products in any suitable manner. For example, they may be reacted with carbon monoxide in the presence of a carbonylation catalyst and then acidified to the corresponding propionic acids as in Gardano et al., Francalanci et al., or Dynamit Nobel; or they may be cyanated and then acidified to the corresponding propionic acids as in Palecek et al. or Tokutake. Another useful synthesis involves reacting the compounds with magnesium, carbonating the resultant Grignard reagents with carbon dioxide, and acidifying the carbonated product to the propionic acid as in Miyatake et al.

The following example is given to illustrate the invention and is not intended as a limitation thereof.

EXAMPLE 1

(COMPARATIVE)
Semi-Batch Operating Mode

1 Sulfuric acid and initial isobutylbenzene (IBB) feed, in the amounts shown in Table I, are charged to the reactor.

2 These materials are circulated in the reactor pump-around loop until they are cooled to the appropriate temperature, while continuously being sparged with hydrogen chloride.

3 Acetaldehyde (AA) and the rest of the isobutylbenzene feed, in the amounts shown in the Table I are charged to the reactor in the time shown in Table I as feed time.

4 The mixture in the reactor is held at the desired temperature for the time shown in Table I to complete the reaction.

5 Reactor pressure is held at 5 psig by venting excess HCl and/or inerts.

6 Periodically samples are taken from the reactor and analyzed to determine the extent of the reaction.

All runs are made with sulfuric acid that had a starting concentration of 93% to 94.5%.

Acetaldehyde and Sulfuric Acid mole ratios shown in Table I are based on total moles of IBB charged.

TABLE I

| Example | IBB Charged (Moles) | | Reactant Mole Ratios | | Reactor Pressure (psig) | Temp (C.) | Feed Time (min) | Total Rxn Time (min) | % Conversion IBB | Yield | | CEBB/DBPE Ratio |
|---|---|---|---|---|---|---|---|---|---|---|---|---|
| | Rxn Feed | Prefeed | AA | H2SO4 | | | | | | CEBB | DBPE | |
| 1-1 | 29.8 | 29.8 | 1.22 | 2.55 | 2.5 | −25 to −20 | 60 | 60 | 26 | 56 | 25 | 4.5 |
| | | | | | | | | 150 | 38 | 62 | 25 | 4.9 |
| 1-2 | 24.2 | 24.2 | 1.22 | 4.00 | 5.0 | −22 to −21 | 87 | 87 | 64 | 31 | 61 | 1.0 |
| | | | | | | | | 240 | 80 | 34 | 59 | 1.2 |
| 1-3 | 32.4 | 32.6 | 1.20 | 4.03 | 5.0 | −26 to −13 | 162 | 158 | 72 | 20 | 73 | 0.6 |
| | | | | | | | | 205 | 85 | 20 | 75 | 0.5 |
| | | | | | | | | 265 | 93 | 17 | 77 | 0.5 |
| 1-4 | 28.1 | 29.8 | 1.22 | 2.75 | 5.0 | −20 to −15 | 71 | 37 | 25 | 55 | 25 | 4.5 |
| | | | | | | | | 80 | 29 | 61 | 21 | 5.8 |
| | | | | | | | | 140 | 34 | 63 | 22 | 5.7 |
| | | | | | | | | 190 | 39 | 66 | 22 | 5.8 |
| | | | | | | | | 255 | 44 | 65 | 23 | 5.6 |
| 1-5 | 25.9 | 29.8 | 1.22 | 2.88 | 5 | −25 to −14 | 105 | 65 | 27 | 56 | 26 | 4.4 |
| | | | | | | | | 110 | 29 | 59 | 24 | 5.0 |
| | | | | | | | | 170 | 32 | 61 | 24 | 5.1 |
| | | | | | | | | 240 | 36 | 62 | 24 | 5.1 |
| | | | | | | | | 290 | 39 | 62 | 25 | 4.9 |
| 1-6 | 29.2 | 29.8 | 1.10 | 2.73 | 5 | −26 to −22 | 178 | 70 | 21.5 | 50.4 | 26.3 | 3.8 |
| | | | | | | | | 140 | 27.7 | 59.5 | 22.5 | 5.3 |
| | | | | | | | | 195 | 27.9 | 60.6 | 21.5 | 5.6 |
| | | | | | | | | 255 | 32.2 | 62.7 | 21.7 | 5.8 |
| | | | | | | | | 315 | 36.4 | 63.2 | 23.1 | 5.5 |
| | | | | | | | | 375 | 37.4 | 60.1 | 26.5 | 4.5 |
| 1-7 | 48.43 | 29.8 | 1.10 | 2.80 | 5 | −25 to −17 | 135 | 18 | 11.2 | 13.7 | 41.8 | 0.7 |
| | | | | | | | | 43 | 20.7 | 37.3 | 38.6 | 1.9 |
| | | | | | | | | 78 | 30.9 | 44.4 | 39.5 | 2.2 |
| | | | | | | | | 143 | 36.7 | 43.3 | 43.1 | 2.0 |
| | | | | | | | | 198 | 43.6 | 42.5 | 46.0 | 1.8 |
| | | | | | | | | 238 | 48.9 | 40.7 | 49.0 | 1.7 |
| 1-8 | 16.6 | 29.8 | 0.64 | 4.42 | 5 | −25 to −17 | 108 | 13 | 8.7 | 9.1 | 33.5 | 0.5 |
| | | | | | | | | 28 | 9.7 | 21.5 | 27.1 | 1.6 |
| | | | | | | | | 58 | 11.0 | 33.3 | 21.3 | 3.1 |
| | | | | | | | | 108 | 11.3 | 37.2 | 18.6 | 4.0 |
| 1-9 | 31.3 | 52.2 | 1.10 | 2.50 | 5 | −29 to −21 | 120 | 15 | 7.1 | 13.7 | 16.2 | 1.7 |
| | | | | | | | | 30 | 9.6 | 31.6 | 16.5 | 3.8 |
| | | | | | | | | 60 | 13.5 | 46.5 | 16.4 | 5.7 |
| | | | | | | | | 105 | 15.6 | 51.4 | 16.5 | 6.2 |
| | | | | | | | | 135 | 15.9 | 49.8 | 18.7 | 5.3 |
| | | | | | | | | 195 | 17.8 | 52.7 | 19.2 | 5.5 |
| | | | | | | | | 255 | 18.9 | 53.2 | 20.3 | 5.2 |
| | | | | | | | | 300 | 20.1 | 54.4 | 20.8 | 5.2 |
| 1-10 | 0 | 83.8 | 1.08 | 2.5 | 5 | −27 to −22 | 120 | 15 | 5.3 | 8.0 | 0.0 | |
| | | | | | | | | 30 | 8.1 | 31.1 | 7.3 | 8.5 |
| | | | | | | | | 60 | 13.1 | 53.4 | 8.4 | 12.7 |
| | | | | | | | | 90 | 17.5 | 60.6 | 10.8 | 11.2 |
| | | | | | | | | 130 | 22.0 | 67.3 | 9.9 | 13.6 |
| | | | | | | | | 205 | 27.4 | 69.6 | 12.2 | 11.5 |
| | | | | | | | | 245 | 30.0 | 70.9 | 12.4 | 11.4 |
| | | | | | | | | 305 | 34.6 | 71.1 | 14.4 | 9.8 |
| 1-11 | 0 | 92.8 | 1.25 | 2.5 | 5 | −27 to −21 | 135 | 15 | 6.2 | 7.8 | 11.0 | 1.4 |
| | | | | | | | | 30 | 8.1 | 18.7 | 19.6 | 1.9 |
| | | | | | | | | 60 | 11.9 | 33.5 | 24.5 | 2.7 |
| | | | | | | | | 90 | 17.0 | 44.8 | 35.9 | 3.5 |
| | | | | | | | | 120 | 20.8 | 49.7 | 26.2 | 3.8 |
| | | | | | | | | 150 | 25.1 | 54.1 | 26.0 | 4.2 |
| | | | | | | | | 210 | 30.7 | 57.7 | 26.0 | 4.4 |

TABLE I-continued

| Example | IBB Charged (Moles) | | Reactant Mole Ratios | | Reactor Pressure (psig) | Temp (C.) | Feed Time (min) | Total Rxn Time (min) | % Conversion IBB | Yield | | CEBB/DBPE Ratio |
|---|---|---|---|---|---|---|---|---|---|---|---|---|
| | Rxn Feed | Prefeed | AA | H2SO4 | | | | | | CEBB | DBPE | |
| | | | | | | | | 270 | 35.9 | 58.6 | 27.5 | 4.3 |
| | | | | | | | | 315 | 40.5 | 59.5 | 18.1 | 4.2 |

CEBB is 1-chloro-1-(4-isobutylphenyl)ethane
DBPE is 1,1-bis(4-isobutylphenyl)ethane
All CEBB and DBPE yields are based an the amount of IBB converted.
DBPE yields are adjusted to account for 2 moles of IBB per mole of DBPE.

EXAMPLE 2

Continuous Operating Mode

1 Sulfuric acid, isobutylbenzene, and acetaldehyde in the amounts shown in Table II as well as excess hydrogen chloride are continuously charged to the reactor while maintaining the reactor temperature in the desired range.

2 Concurrently with the feed of reactants as described above, a portion of the mixture in the reactor is continuously removed from the reactor in such an amount to hold the total volume of material in the reactor constant.

3 The feed rates and product removal rates are adjusted as required to obtain the residence times shown in Table II.

4 Periodically samples are taken from the reactor and analyzed to determine the extent of the reaction.

All runs are made with sulfuric acid that had a starting concentration of 93% to 94.5%.

Acetaldehyde and Sulfuric Acid mole ratios shown in Table II are based on total moles of IBB charged.

TABLE II

| Example | Reactant Mole Ratios | | | Reactor Pressure (psig) | Temp (C.) | Residence Time (min) | Sample Time (min) | % Conv IBB | % Yield | | CEBB/DBPE Ratio |
|---|---|---|---|---|---|---|---|---|---|---|---|
| | IBB | AA | H2SO4 | | | | | | CEBB | DBPE | |
| 2-1 | 1.00 | 1.20 | 2.53 | 5.0 | −25 to −21 | 120 | 58 | 14.1 | 67.2 | 30.6 | 4.4 |
| | | | | | | | 148 | 15.8 | 74.4 | 23.3 | 6.4 |
| | | | | | | | 208 | 18.1 | 76.3 | 21.3 | 7.2 |
| | | | | | | | 268 | 21.1 | 77.6 | 20.0 | 7.8 |
| | | | | | | | 333 | 23.8 | 78.7 | 18.9 | 8.3 |
| | | | | | | | 388 | 26.6 | 79.4 | 18.4 | 8.6 |
| | | | | | | | 448 | 28.8 | 79.0 | 18.8 | 8.4 |
| | | | | | | | 503 | 31.7 | 79.5 | 18.3 | 8.7 |
| 2-2 | 1.00 | 1.49 | 3.59 | 5.0 | −20 to −16 | 120 | 65 | 14.5 | 68.2 | 29.6 | 4.6 |
| | | | | | | | 120 | 16.3 | 74.3 | 23.5 | 6.3 |
| | | | | | | | 180 | 21.3 | 77.9 | 19.9 | 7.8 |
| | | | | | | | 240 | 25.9 | 79.1 | 18.6 | 8.5 |
| | | | | | | | 300 | 32.0 | 80.2 | 17.6 | 9.1 |
| | | | | | | | 360 | 34.0 | 80.3 | 17.6 | 9.2 |
| | | | | | | | 420 | 37.5 | 80.2 | 17.6 | 9.1 |
| | | | | | | | 465 | 40.8 | 79.7 | 18.0 | 8.8 |
| 2-3 | 1.00 | 1.57 | 3.26 | 5.0 | −25 | 120 | 60 | 41.5 | 48.3 | 50.3 | 1.9 |
| | | | | | | | 180 | 36.0 | 65.7 | 32.4 | 4.1 |
| | | | | | | | 240 | 37.8 | 69.6 | 28.5 | 4.9 |
| | | | | | | | 300 | 35.8 | 72.8 | 25.2 | 5.8 |
| | | | | | | | 360 | 33.1 | 74.2 | 23.7 | 6.3 |
| | | | | | | | 420 | 29.6 | 75.7 | 22.3 | 6.8 |
| | | | | | | | 480 | 26.6 | 77.1 | 20.8 | 7.4 |
| | | | | −25 | 240 | 545 | 24.6 | 77.4 | 20.5 | 7.6 |
| | | | | | | | 600 | 21.6 | 77.4 | 20.4 | 7.6 |
| | | | | | | | 655 | 30.9 | 80.0 | 17.9 | 9.0 |
| | | | | | | | 725 | 33.4 | 80.8 | 17.0 | 9.5 |
| | | | | | | | 780 | 35.8 | 81.5 | 16.3 | 10.0 |
| | | | | | | | 835 | 36.4 | 81.3 | 16.5 | 9.9 |
| | | | | | | | 895 | 37.1 | 81.4 | 16.4 | 10.0 |
| | | | | | | | 950 | 38.1 | 81.1 | 16.7 | 9.7 |
| | | | | | | | 1,010 | 42.6 | 81.2 | 16.6 | 9.8 |
| | | | | −20 | 240 | 1,070 | 46.5 | 80.9 | 16.9 | 9.5 |
| | | | | | | | 1,130 | 49.5 | 80.5 | 17.4 | 9.3 |
| | | | | | | | 1,190 | 51.6 | 79.8 | 18.0 | 8.8 |
| | | | | | | | 1,250 | 52.9 | 79.2 | 18.7 | 8.5 |
| | | | | | | | 1,310 | 54.0 | 78.6 | 19.3 | 8.1 |
| | | | | | | | 1,370 | 55.3 | 77.9 | 20.0 | 7.8 |
| | | | | | | | 1,430 | 56.0 | 77.4 | 20.6 | 7.5 |
| | | | | | | | 1,490 | 56.6 | 76.7 | 21.3 | 7.2 |
| | | | | | | | 1,550 | 57.8 | 75.8 | 22.2 | 6.8 |
| | | | | | | | 1,610 | 55.9 | 74.4 | 23.7 | 6.3 |

CEBB is 1-chloro-1-(4-isobutylphenyl)ethane
DBPE is 1,1-bis(4-isobutylphenyl)ethane
All CEBB and DBPE yields are based on the amount of IBB converted.
DBPE yields are adjusted to account for 2 moles of IBB per mole of DBPE.

It is obvious that many variations may be made in the products and processes set forth above without departing from the spirit and scope of this invention.

What is claimed is:

1. A process for producing an aryl-substituted ethylhalide having the formula

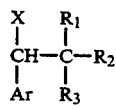

where X is halo; Ar is phenyl, substituted phenyl, naphthyl or substituted naphthyl; $R_1$, $R_2$, and $R_3$ are the same or different and are hydrogen, alkyl, phenylalkyl or substituted phenylalkyl, comprising
   a) continuously adding with agitation an aromatic compound having at least one free ring position to from about 0.1 to about 2.0 mol of an aldehyde of the formula

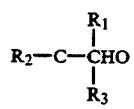

per mol of said aromatic compound in the presence of from about 0.1 to about 2.0 moles of a halo acid per mol of said aromatic compound and about 2-15 moles of hydrogen sulfate per mol of said aromatic thereby forming a reaction mixture;
   b) continuously removing from said reaction mixture a reaction effluent stream at a rate substantially equal to the sum of the rates of addition of said aromatic compound; said aldehyde; said haloacid; and said hydrogen sulfate; and
   c) separating from said reaction effluent stream said aryl-substituted ethyl halide, said separation being carried out when the ratio of the concentration of said aryl-substituted ethyl halide to the concentration of the by-products of said process and the concentration of aryl-substituted ethyl halide becomes constant.

2. The process of claim 1 wherein the aromatic compound is monoalkylbenzene.

3. The process of claim 2 wherein the monoalkylbenzene is one in which the alkyl substituent contains 1-5 carbons.

4. The process of claim 3 wherein the monoalkylbenzene is isobutylbenzene.

5. The process of claim 1 wherein the aldehyde is one in which $R_1$ is an alkyl group containing 1-10 carbons and $R_2$ and $R_3$ are the same as $R_1$ or hydrogen.

6. The process of claim 5 wherein the aldehyde is one in which $R_1$ is an alkyl group containing 1-6 carbons and $R_2$ and $R_3$ are hydrogen.

7. The process of claim 6 wherein the aldehyde is one in which $R_1$ is alkyl having 1 to 3 carbons.

8. The process of claim 7 wherein $R_1$ is methyl.

9. The process of claim 1 wherein the amount of about one molecule of aldehyde is employed per mole of aryl-substituted ethyl halide produced.

10. The process of claim 1 wherein the reaction temperature is in the range of about $-35°$ C. to about $-15°$ C.

11. The process of claim 10 wherein the reaction temperature is in the range of about $-30°$ C. to about $-20°$ C.

12. The process of claim 1 wherein the amount of hydrogen sulfate is about 2-6 moles per mol of aromatic compound.

13. The process of claim 1 wherein the hydrogen sulfate is introduced into the reaction mixture in the form of 88-98% sulfuric acid or in the form of oleum.

14. The process of claim 1 wherein the reaction is conducted in the absence of more than about 15% by weight of water, based on the weight of the hydrogen sulfate.

15. The process of claim 1 wherein the hydrogen chloride is introduced by bubbling it through the reaction mixture.

16. The process of claim 1 wherein the hydrogen chloride is introduced by pressurizing the reaction vessel with it.

17. The process of claim 1 wherein the hydrogen chloride is introduced as a liquid to the reaction vessel.

18. The process of claim 1 wherein one molar proportion of isobutylbenzene is chloroethylated by reacting it with at least about 0.1 molar proportions of acetaldehyde at a temperature in the range of about $-30°$ C. to about $-20°$ C. in the presence of about 2-6 molar proportions of hydrogen sulfate per mole of aromatic compound with less than about 15% by weight of water, based on the weight of the hydrogen sulfate, while bubbling hydrogen chloride through the reaction mixture or pressurizing the reaction vessel with hydrogen chloride; the hydrogen sulfate being introduced in the form of 88-98% sulfuric acid.

19. The process of claim 1 wherein one molar proportion of isobutylbenzene is chloroethylated by reacting it with at least about two molar proportions of acetaldehyde at a temperature in the range of about $-30°$ C. to about $-20°$ C. in the presence of about 2-6 molar proportions of hydrogen sulfate per mole of aromatic compound with less than about 15% by weight of water, based on the weight of the hydrogen sulfate, while adding an aqueous solution of hydrogen chloride; hydrogen sulfate being introduced in the form of 88-98% sulfuric acid.

* * * * *